United States Patent
Cassady et al.

(10) Patent No.: US 7,838,519 B2
(45) Date of Patent: Nov. 23, 2010

(54) MAYTANSINOID ANALOGS AS ANTITUMOR AGENTS

(75) Inventors: John M. Cassady, Corvallis, OR (US); Heinz G. Floss, Bellevue, WA (US)

(73) Assignee: The Ohio State University Research Foundation, Columbus, OH (US)

( * ) Notice: Subject to any disclaimer, the term of this patent is extended or adjusted under 35 U.S.C. 154(b) by 516 days.

(21) Appl. No.: 10/599,930

(22) PCT Filed: Apr. 4, 2005

(86) PCT No.: PCT/US2005/011441

§ 371 (c)(1),
(2), (4) Date: Apr. 25, 2008

(87) PCT Pub. No.: WO2005/099754

PCT Pub. Date: Oct. 27, 2005

(65) Prior Publication Data

US 2008/0249085 A1    Oct. 9, 2008

Related U.S. Application Data

(60) Provisional application No. 60/562,119, filed on Apr. 14, 2004.

(51) Int. Cl.
*C07D 498/18*    (2006.01)
*A61K 31/55*    (2006.01)
*A61P 35/00*    (2006.01)

(52) U.S. Cl. .............. 514/229.5; 514/229.8; 540/456
(58) Field of Classification Search ............... 540/456; 514/229.5, 229.8
See application file for complete search history.

(56) References Cited

U.S. PATENT DOCUMENTS 4,364,866 A    12/1982    Asai et al.

FOREIGN PATENT DOCUMENTS

JP          58167592        * 10/1983
WO    WO 2005/099754        10/2005

OTHER PUBLICATIONS

Spiteller et al. (Journal of the American Chemical Society (2003), 125(47), 14236-14237).*
Cassady et al., "Recent Developments in the Maytansidnoid Antitumor Agents", Chem. Pharm. Bull, 52 (1): Jan. 1-26, 2004.
Kupchan, S.M. et al. "Maytansine, a Novel Antileukemic Ansa Macrolide from *Maytenus ovatus*", J. Am. Chem. Soc. vol. 94, p. 1354-1356, 1972.

* cited by examiner

*Primary Examiner*—Bruck Kifle
(74) *Attorney, Agent, or Firm*—Calfee, Halter & Griswold LLP

(57) ABSTRACT

Ansamycin analogs, including maytansinoid analogs, and their use in treating cell proliferative diseases and conditions, and in particular, for use as antitumor agents.

7 Claims, No Drawings

MAYTANSINOID ANALOGS AS ANTITUMOR AGENTS

DESCRIPTION OF THE INVENTION

This application claims priority to U.S. Provisional Application No. 60/562,119, filed Apr. 14, 2004.

FIELD OF THE INVENTION

The present invention relates to ansamycin analogs, including maytansinoid analogs, and their use in treating cell proliferative diseases and conditions, and in particular, for use as antitumor agents.

BACKGROUND OF THE INVENTION

The report by Kupchan and coworkers in 1972 on the bioassay-guided isolation of the potent cytotoxic agent, maytansine from the Ethiopian shrub, *Maytenus serrata*, raised high hopes for its eventual use as a chemotherapeutic agent for the treatment of cancer. However, clinical trials with maytansine proved disappointing, showing no significant clinical benefits from its administration to human cancer patients. Nevertheless, because of their extremely high potency, maytansine and its congeners continue to command interest.

It is accordingly a primary object of the invention to provide new maytansinoid analogs with improved antitumor activity.

SUMMARY OF THE INVENTION

Features and Advantages of the Invention

The invention is advantageous in providing improved maytansinoid compounds with lower systemic toxicity, improved pharmacokinetic profile, and better clinical activity.

SUMMARY OF THE INVENTION

In accordance with the invention, novel maytansinoid analogs are provided.

The invention is directed to, for example, antitumor compounds having the following structure:

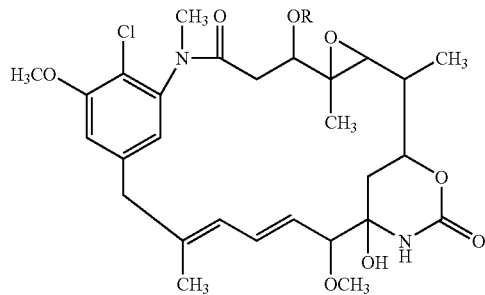

wherein R is chosen from:
Formula I: $CH_2COCH(CH_3)_2$,
Formula II: $CH_2CO(CH_2)_{16}CH_3$, and
Formula III: $CH_2COCH(NH_2)Ph$.

The present invention is also directed to antitumor compounds having structures similar to:

(Formula IV)

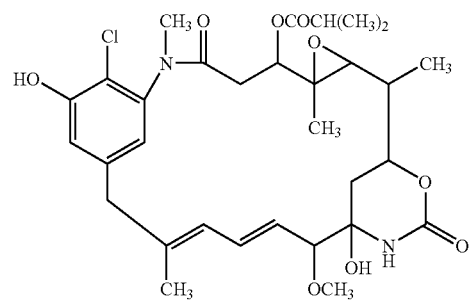

The present invention is also directed to antitumor compounds having the following structure:

(Formula V)

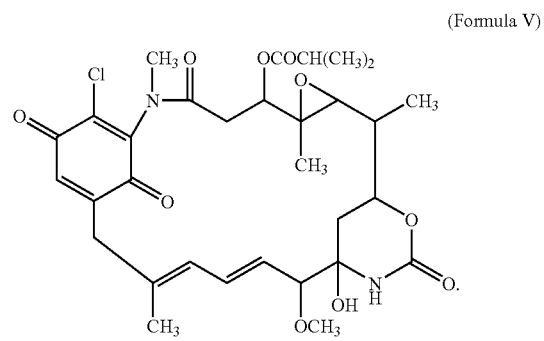

The present invention is also directed to antitumor compounds having the following structure:

(Formula VI)

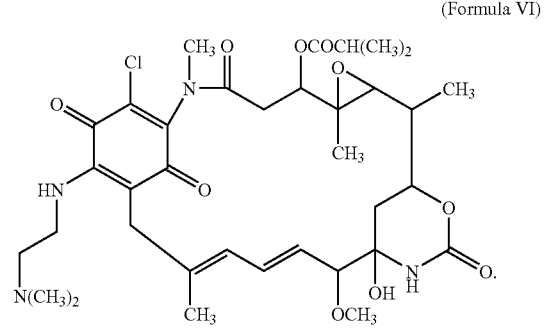

The present invention is also directed to antitumor compounds having the following structure:

(Formula VII)

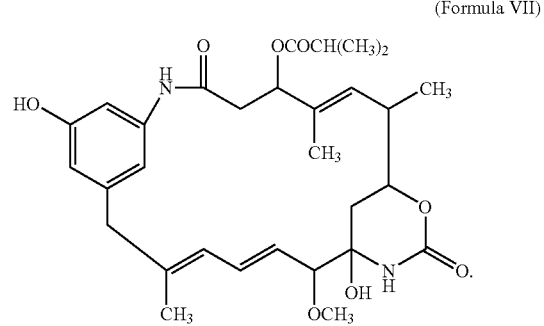

The present invention is also directed to antitumor compounds having the following structure:

(Formula VIII)

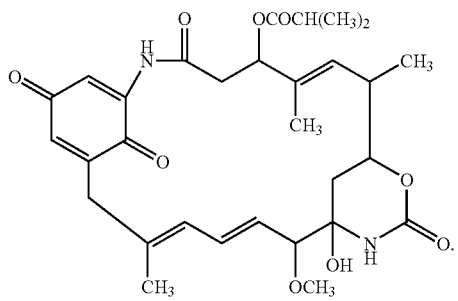

The present invention is also directed to antitumor compounds having the following structure:

(Formula IX)

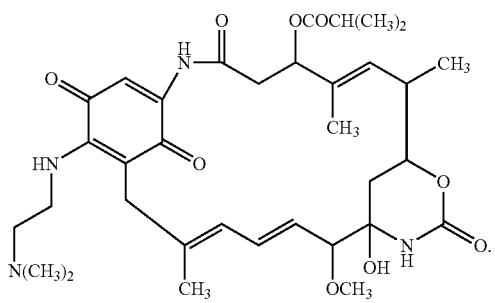

Additional features and advantages of the invention will be set forth in part in the description that follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE EMBODIMENTS

Reference will now be made in detail to specific embodiments (exemplary embodiments) of the invention. Throughout this disclosure, reference will be made to compounds according to the invention. Reference to such compounds, in the specification and claims, includes esters and salts of such compounds. Thus, even if not explicitly recited, such esters and salts are contemplated, and encompassed, by reference to the compounds themselves.

As used herein, the term "hydrocarbyl" includes, but is not limited to, "aliphatic," "cycloaliphatic," and "aromatic" groups. Thus, hydrocarbyl groups include, but are not limited to, alkyl, alkenyl, alkynyl, cycloalkyl, aryl, aralkyl, and alkaryl groups. Further, "hydrocarbyl" is understood to include both non-substituted hydrocarbyl groups, and substituted hydrocarbyl groups, with the latter referring to the hydrocarbon portion bearing additional substituents, besides carbon and hydrogen.

The present invention is generally directed to novel compounds having structures related to the maytansinoid group, and in some cases, to the geldanamycin group, and to methods of use of these compounds in the treatment of cell proliferative diseases and conditions. Maytansinoids generally target tubulin, whereas geldanamycins generally target heat shock protein-90 (HSP-90). Compounds of the present invention can target tubulin, HSP-90, or both, and can exhibit a cytotoxic effect through one or both of these mechanisms.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In some embodiments, the invention provides a method for inhibiting neoplastic cell proliferation in an animal comprising administering to an animal having at least one neoplastic cell present in its body a therapeutically effective amount of a compound of the invention. Cancers treatable according to the invention include, but are not limited to, prostate cancer, lung cancer, acute leukemia, multiple myeloma, bladder carcinoma, renal carcinoma, breast carcinoma, colorectal carcinoma, neuroblastoma, or melanoma. Other diseases treatable with the present compounds include fungal infections or infestations; the present compounds can be used for any control of fungal growth.

Work with maytansine has been disappointing due to dose-limiting toxicity in humans. However, the fact that animal tests have proved effective suggests that the problem lies in differences in metabolism. Thus, without wishing to be bound by any particular theory, the present invention strives to improve clinical effects of these compounds by changing the manner in which they are metabolized. The effect is to produce compounds with reduced toxicity but better clinical efficacy.

The compounds of the invention include, but are not limited to, two major groups. Group I includes non-hydrolyzable esters (analogs) of ansamitocin P-3 (AP3) or maytansine. The ester moiety is believed to be important for tubulin binding and cytotoxicity. Although metabolism and pharmacokinetic studies are still in progress, it is clear that the ester is modified and is susceptible to decomposition with time.

The second major group of compounds include hybrid molecules that incorporate the potential to target both tubulin (a maytansinoid quality) and HSP-90 (a geldanamycin quality). These hybrid analogs can be generally referred to as "geldanamitocins."

Group I compounds (e.g., the "non-hydrolyzable" analogs) can be synthesized by any method that will yield the compounds as described herein. One example of a method that can be used involves the reductive cleavage of ansamitocin P-3 to yield maytansinol:

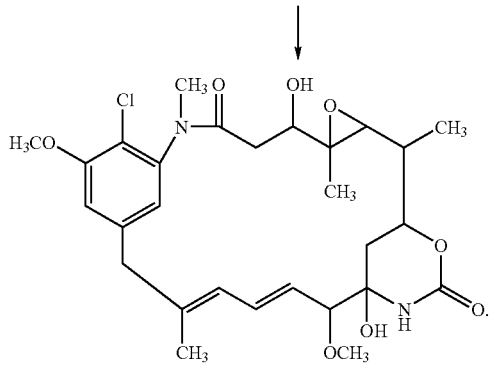

The arrow indicates the site of reaction.

Maytansinol is reacted (at the C(3) hydroxyl) with R—COCH$_2$Cl to yield:

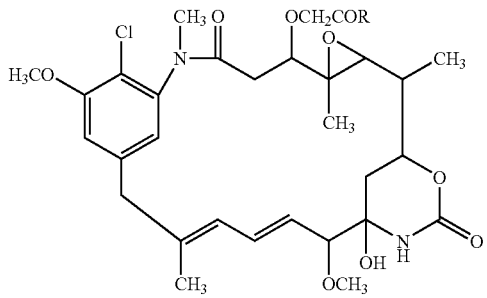

wherein R comprises any hydrocarbyl group. Other examples of R include but are not limited to:

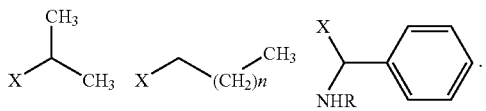

Where n is from 1 to about 20. (X refers to the remainder of the molecule.)

If the reaction at the C(3) hydroxyl (shown by the arrow in the maytansinol structure above) is not feasible, then other targets can be designed, including, for example:

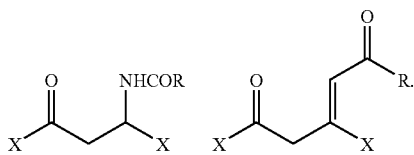

Again, the X refers to the remainder of the maytansinol structure and R is as described above.

Compounds of Group II can be synthesized by transforming AP3 into 20-O-demethyl-AP3, for example, through use of *Bacillus megaterium* IFO 12108. The demethyl-AP3 can then be oxidized to the quinone through numerous of reactions. The quinone can then be converted into the 17-DMAG analog by addition of, for example, 2-N,N-dimethylaminoethylamine.

Other aspects of the invention relate to improving the ansamitocin production yield of *Actinosynnema pretiosum* by genetically manipulating the regulatory controls of ansamitocin biosynthesis and/or by gene shuffling.

A review of the maytansinoid compounds as anti-tumor agents is presented in "Recent Developments in the Maytansinoid Antitumor Agents," by Cassady et al., *Chem. Pharm. Bull.* 52(1): 1-26 (January 2004). The entire disclosure of the Cassady et al. review article is incorporated herein by reference.

EXAMPLES

Example 1

Non-Hydrolyzable Ester Analogs of AP3 and their Antitumor Activity

Ansamitocin P-3 (AP3) is reduced with Li(OMe)$_3$AlH to produce maytansinol. Chloromethylketone derivatives are prepared from isobutyric acid, hexadecanoic acid, and phenylglycine, respectively, by conversion to acid chloride (which may require N-protection in the case of phenylglycine), reaction with diazomethane, and reaction of the diazoketone with HCl.

Maytansinol is reacted with the three chloroketones to produce the analogs of Formulas I, II and III:

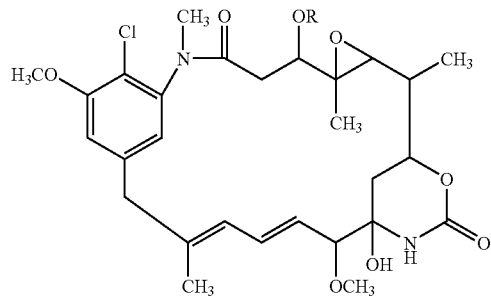

wherein R is chosen from:
Formula I: CH$_2$COCH(CH$_3$)$_2$,
Formula II: CH$_2$CO(CH$_2$)$_{16}$CH$_3$, and
Formula III: CH$_2$COCH(NH$_2$)Ph.

The three analogs are tested for cytotoxicity in appropriate cancer cell lines and in a tubulin binding assay.

Example 2

Production of Maytansinoid-Geldanamycin Hybrid-Type Molecules

In this Example, hybrid molecules are constructed that combine the mode of action of maytansinoids, i.e., inhibition of tubulin polymerization, with that of geldanamycin, i.e., inhibits heat shock protein 90 (HSP-90). In particular, the hybrid molecules retain the cyclic carbinolamide structure of the ansamitocins.

Biotransformation of AP3 is carried out using *Bacillus megaterium* IFO 12108 to produce 20-O-demethyl-AP3 (this procedure is known in the art and has been described in detail elsewhere):

(Formula IV)

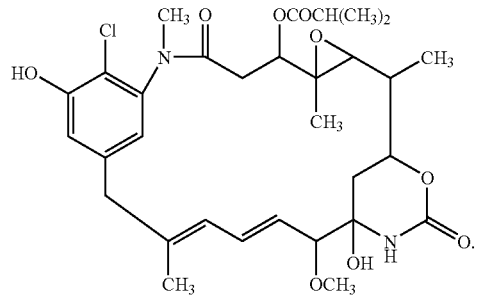

The compound of Formula IV is then oxidized to yield the quinone:

(Formula V)

The quinone (Formula V) is then converted into the 17-DMAG analog (Formula VI) by addition of 2-N,N-dimethylaminoethylamine.

(Formula VI)

The compounds of Formulas IV, V, and VI are then tested for tubulin binding and for HSP-90 binding, as well as for cytotoxicity.

Example 3

Preparation and Testing of Additional Analogs

This Example describes the preparation and testing of additional analogs.

A mutant of *Actinosynnema pretiosum* is engineered in which genes asm7, 10, 11, and 12 have been deleted. The genotype is then confirmed.

The mutant is fermented and cultures are assayed for production of deschloro-20-O-demethyl-N-demethyl-desepoxy-AP3:

(Formula VII)

The compound of Formula VII is oxidized to the quinone of Formula VIII:

(Formula VIII)

The quinone (Formula VIII) is derivatized to yield the 17-DMAG analog:

(Formula IX)

Compounds VII, VIII, and IX are tested for general cytotoxicity, for HSP-90 binding, and for tubulin binding.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise defined, all technical and scientific terms used herein have the same meaning as commonly understood by one of the ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. A compound having the following structure:

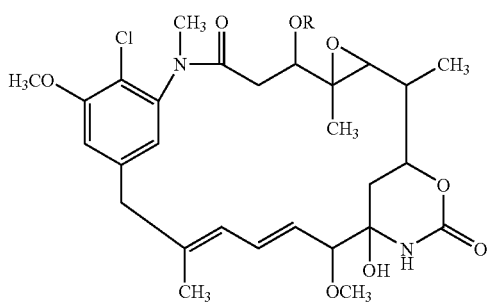

wherein R is chosen from:
I: $CH_2COCH(CH_3)_2$,
II: $CH_2CO(CH_2)_{16}CH_3$, and
III: $CH_2COCH(NH_2)Ph$.

2. A compound having the following structure:

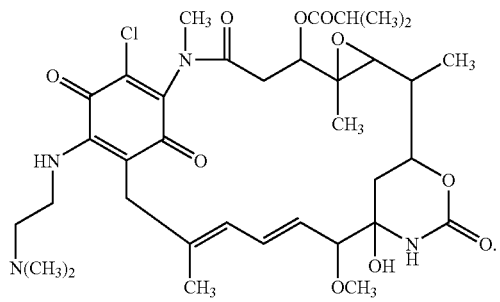

3. A compound having the following structure:

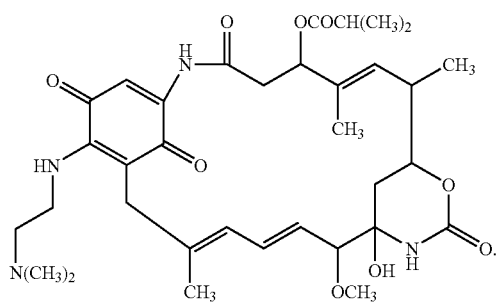

4. A compound having the following structure:

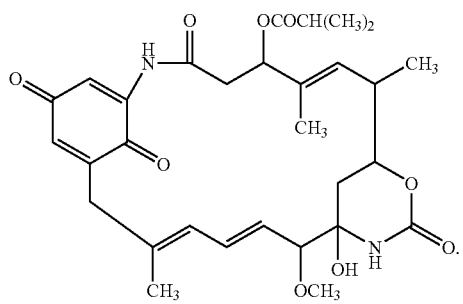

5. A compound having the following structure:

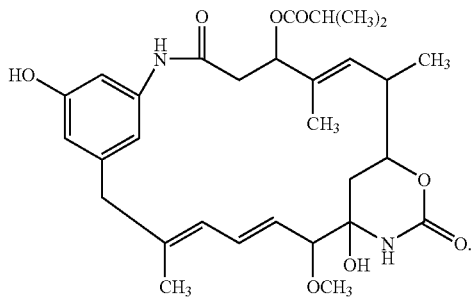

6. A method for treating a cancer selected from the group consisting of prostate cancer, lung cancer, acute leukemia, multiple myeloma, bladder carcinoma, renal carcinoma, colorectal carcinoma, neuroblastoma, and melanoma comprising administering to an animal in need thereof a therapeutically effective amount of at least one compound according to any one of claim 1 or 2-5.

7. A method of inhibiting fungal growth comprising administering to an animal in need thereof a therapeutically effective amount of at least one compound according to any one of claim 1 or 2-5.

* * * * *